United States Patent [19]
Lee

[11] Patent Number: 4,776,835
[45] Date of Patent: Oct. 11, 1988

[54] SWAB MANIPULATOR

[76] Inventor: Freddy T. Lee, 2008 SW. 17 St., Boynton Beach, Fla. 33435

[21] Appl. No.: 59,255

[22] Filed: Jun. 3, 1987

[51] Int. Cl.⁴ .............................................. A61F 2/06
[52] U.S. Cl. ........................................ 604/1; 128/67; 604/309
[58] Field of Search ................. 128/56, 67, 303; 604/1–3, 11, 47, 289, 309; 401/6

[56] References Cited
U.S. PATENT DOCUMENTS

| | | | |
|---|---|---|---|
| 1,525,158 | 2/1925 | Viol | 604/309 X |
| 1,525,166 | 2/1925 | Cameron | 604/309 X |
| 3,568,237 | 3/1971 | Rhodes | 401/6 X |

Primary Examiner—Allen M. Ostrager
Attorney, Agent, or Firm—Victor F. Volk

[57] ABSTRACT

A manipulator is described to apply a double ended cotton swab to a person's back. The manipulator has a groove which holds the swab rod in a slide grip, and a blocking protrusion that restrains the swab from sliding.

10 Claims, 1 Drawing Sheet

U.S. Patent  Oct. 11, 1988  4,776,835
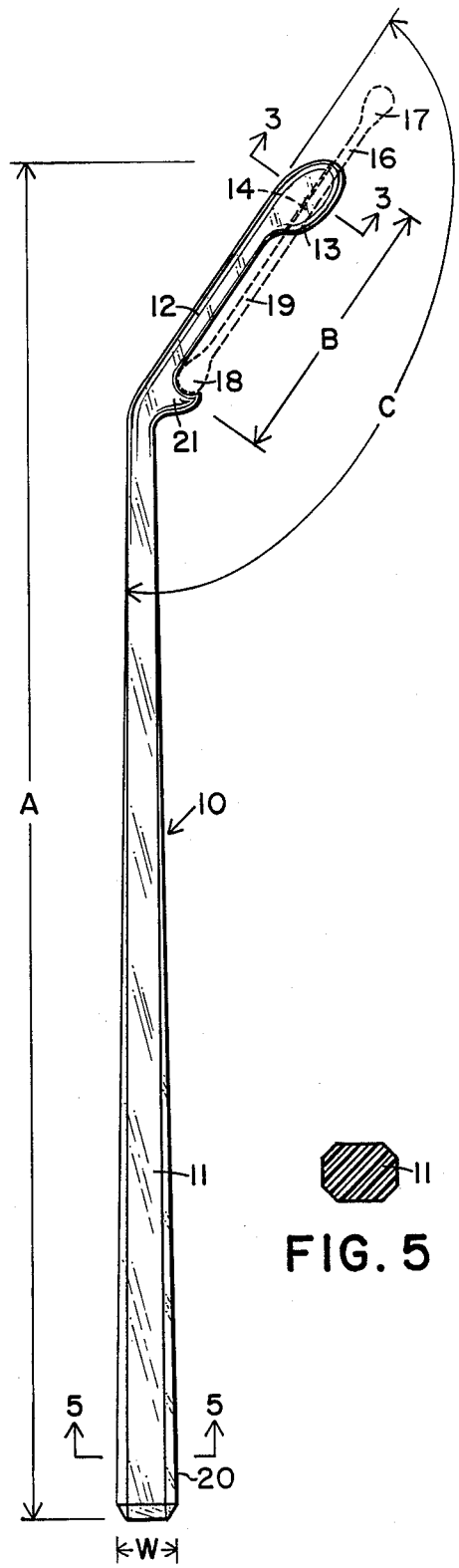
FIG. 1
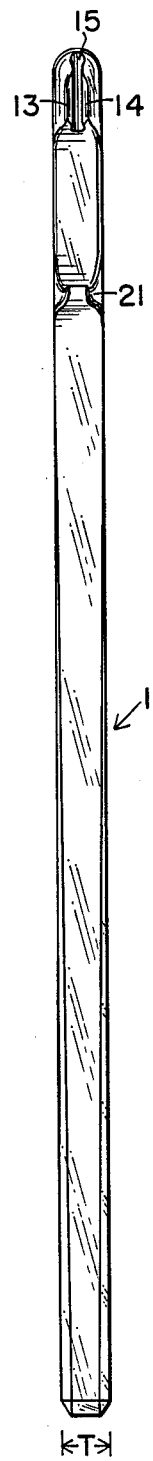
FIG. 2
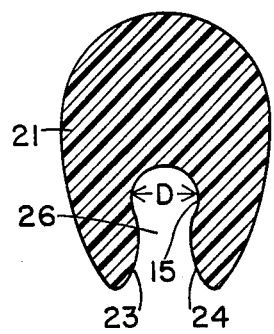
FIG. 3
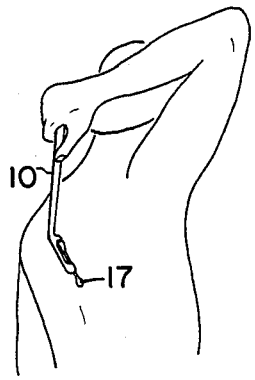
FIG. 4
FIG. 5
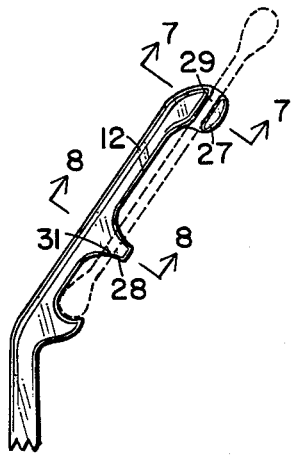
FIG. 6
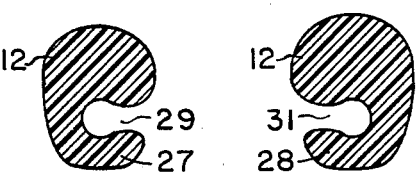
FIG. 7  FIG. 8

SWAB MANIPULATOR

BACKGROUND OF THE INVENTION

Cotton swabs are widely available in standard 3-inch (7.62 cm) rod lengths and 1/10-inch (2.54 mm) rod diameter, with the cotton factory-applied at both ends of the rod. It is a purpose of the present invention to enable a person to use such swabs, unassisted, to apply medication accurately to portions of his person, such as his back, which would otherwise be difficult or impossible to reach.

In a professional search of the Patent and Trademark Office files U.S. Pat. Nos. 1,431,881 to Eriscon-Smith and 4,381,766 to Avollo were developed on devices enabling a person to apply powder or fluid to his or her back. But neither of these patents would be useful for the purpose of the present invention since they do not describe or suggest devices capable of manipulating a swab, and particularly a double ended swab. The search also developed U.S. Pat. No. 4,283,809 to Prost which describes a swab holder for cleaning apparatus and the like with single-ended swabs. Prost's device would be useless for a double-ended swab since it is necessary to insert an end of the rod of the swab into a close-fitting tube. Nor could the Prost device direct a swab at the proper angle for application by someone to his own back.

SUMMARY OF THE INVENTION

My swab manipulator comprises an elongated handle member with a relatively short extension at an obtuse angle. The extension comprises walls that project to define a swab-engaging groove, and a blocking member extends from my manipulator so as to block lengthwise movement of the swab that is being held in the groove.

Advantageously, the projecting walls are substantially parallel and define a groove between them, but will taper enough to form a restricted entrance portion to the groove, into which the rod of a swab can be introduced and removed sideways rather than endwise.

In one embodiment my manipulator comprises first and second groove-defining walls spaced longitudinally from each other, grooves being formed between these walls and the extension itself. Advntageously. also, the handle member is polygonal in section with a width that differs from its thickness, and the handle tapers toward the extension.

For handling standard swabs my groove should confine a rod about 1/10 inch in diameter and the blocking member should be about 2¼ inches from a free end of the extension. Advantageously, the extension will form an angle of about 145 degrees with the remainder of the handle member.

BRIEF DESCRIPTION OF THE DRAWING

FIG. 1 shows a side view of my manipulator.

FIG. 2 shows a front view of the manipulator of FIG. 1.

FIG. 3 shows an enlarged section through the lines 3—3 of FIG. 1.

FIG. 4 shows a pictorial view of the manipulator of FIG. 1 being used to apply medication to a person's back.

FIG. 5 shows a section through the lines 5—5 of FIG. 1.

FIG. 6 shows a partial side view of another embodiment of my invention.

FIG. 7 shows an enlarged section through the lines 7—7 of FIG. 6.

FIG. 8 shows an enlarged section through the lines 8—8 of FIG. 6.

DETAILED DESCRIPTION OF PREFERRED EMBODIMENT

Referring first to FIG. 1 my manipulator 10 has a slender, elongated handle 11, tapered upwardly toward an extension 12 that is bent at an angle C of 145 degrees to the handle 11. A projecting portion of the extension 12 takes the form of two wall portions 13, 14 which define a lengthwise groove 15 (FIG. 3) with a diameter D that forms a slide fit with the rod 16 of a prefabricated swab 19 that has cotton twists 17, 18 at either end. Manipulator 10 is fabricated of a translucent, smooth-surfaced polymeric resin which is attractive and easy to keep clean, and can be economically cast or molded in volume. My invention is not limited, however to the use of this particular material, and wood or glass, for example, might be used within its scope. The handle 11 tapers from its lower end 20 to the section where it forms the extension 12, and is octagonal in section see (FIG. 5) so that it can be easily twisted and oriented by the fingers of a person who is treating his back and does not have the manipulator in his sight. The taper, too, aids in finger gripping by a person with his hand behind his back as is made clear in FIG. 4. Orienting is also aided by the fact that the handle 11 is wider than it is thick, the dimension W of FIG. 1 being greater than the dimension T of FIG. 2.

The lower end of the extension 12 comprises a projecting blocking member 21 that extends in the same direction as the extension formed by the wall portions 13, 14 and constitutes a stop or block for the swab 19. Referring now to FIG. 3 the section of the groove 15 is shown in an enlarged view to comprise tapering entrance walls 23, 24 terminating in a constriction 26 that permits a rod to be pressed through to the groove 15 proper but will confine it there. The diameter D of the groove 15 is such that a rod 16 will have a slide fit. In the illustrated example the diameter D is about 1/10 inch (2.54 mm), and the width of the constriction 26 is about 0.25 mm less. The length of the groove 15 is about ¾ inch (19 mm) which provides a firm grip for holding the swab.

The distance B (FIG. 1) between the blocking member 21 and the end of the walls 13,14 is about 2174 inches (5.7 mm) which provides that the cotton twist 17 will project about ¾ inch (19 mm) for a standard 3-inch swab, and the overall length A is about 11.5 inches (29 cm).

In FIGS. 6-8 I have shown an embodiment of my manipulator in which the walls 13, 14 are replaced by spaced-apart walls 27, 28 which are connected to opposite sides of the extension 12 whereby grooves 29, 31 are formed between the respective walls 27, 28 and the extension 12, and entrance to the grooves 29, 31 are from opposite sides so that the swab will be inserted by twisting. This alternative structure has an advantage in simplifying the molds in which the manipulators are cast.

Although I have illustrated the use of my manipulator with double ended swabs it is evident that it can be used equally well with a swab that has only one cotton twist. However, my invention has particular utility for the double ended swabs since it provides a unique means of gripping such rods by snapping them into the groove 15 while still providing finger grasping means between the walls 13, 14 and the blocking member 21 to pull the swabs out again. It should be noted that, although my manipulator has particular utility for applying medicaments, such as iodine, to ones person it performs very well where swabs are used to dry or clean electrical apparatus, typewriters and the like.

The foregoing description has been exemplary rather than definitive of my invention for which I desire an award of Letters Patent as defined in the appended claims.

I claim:

1. a swab manipulator comprising:
   (A) an elongated handle member, and a relatively short extension thereof, said handle member and said extension comprising an obtuse angle therebetween,
   (B) walls projecting from said extension defining a swab-engaging groove,
   (C) a blocking member extending from said handle so as to block lengthwise movement of said swab.

2. The swab manipulator of claim 1 wherein said walls are substantially parallel and define said groove between them.

3. The swab manipulator of claim 2 wherein said walls taper to define a constricted entrance portion to said groove.

4. The swab manipulator of claim 1 comprising first and second of said walls, said first wall being spaced longitudinally from said second wall and said groove being formed between each of said walls and said extension.

5. The swab manipulator of claim 1 wherein said handle member is tapered toward said extension.

6. The swab manipulator of claim 1 wherein said handle member is polygonal in section.

7. The swab manipulator of claim 1 wherein said said groove confines swab rods having diameters of about 1/10 inch (2.54 mm).

8. The swab manipulator of claim 1 wherein said second projecting portion is spaced about 2174 inches (5.7 cm) from a free end of said extension, whereby said manipulator will accommodate standard 3-inch swabs.

9. The manipulator of claim 1 wherein said obtuse angle is about 145 degrees.

10. The manipulator of claim 6 comprising a width and a thickness of said handle member of substantially unequal dimensions.

* * * * *